US008026378B2

(12) United States Patent
Selifonov

(10) Patent No.: US 8,026,378 B2
(45) Date of Patent: Sep. 27, 2011

(54) GLYCERYL ETHER COMPOUNDS AND THEIR USE

(75) Inventor: Sergey Selifonov, Plymouth, MN (US)

(73) Assignee: Segetis, Inc., Golden Valley, MN (US)

( * ) Notice: Subject to any disclaimer, the term of this patent is extended or adjusted under 35 U.S.C. 154(b) by 550 days.

(21) Appl. No.: 11/994,483

(22) PCT Filed: Nov. 22, 2006

(86) PCT No.: PCT/US2006/045191
§ 371 (c)(1),
(2), (4) Date: Jun. 2, 2008

(87) PCT Pub. No.: WO2007/062112
PCT Pub. Date: May 31, 2007

(65) Prior Publication Data
US 2010/0222603 A1 Sep. 2, 2010

Related U.S. Application Data

(60) Provisional application No. 60/738,987, filed on Nov. 22, 2005.

(51) Int. Cl.
*C07D 317/18* (2006.01)
(52) U.S. Cl. ...................................... 549/448
(58) Field of Classification Search .................. 549/448
See application file for complete search history.

(56) References Cited

U.S. PATENT DOCUMENTS

| 4,465,866 | A | | 8/1984 | Takaishi et al. |
|---|---|---|---|---|
| 5,362,494 | A | * | 11/1994 | Zysman et al. |
| 5,442,082 | A | | 8/1995 | Uphues et al. |
| 5,539,001 | A | * | 7/1996 | Waldmann-Laue et al. |
| 5,627,144 | A | | 5/1997 | Urfer et al. |
| 6,211,329 | B1 | | 4/2001 | Rehnberg et al. |
| 2003/0167681 | A1 | | 9/2003 | Puche |
| 2004/0077904 | A1 | | 4/2004 | Nagasawa et al. |

FOREIGN PATENT DOCUMENTS

| EP | 0524548 | * | 1/1993 |
|---|---|---|---|
| JP | 54145224 | | 11/1979 |
| JP | 4217972 | | 8/1992 |
| JP | 2007/016018 | * | 1/2007 |
| WO | WO1992/008685 A1 | | 5/1992 |

OTHER PUBLICATIONS

Biswas et al., "Synthesis of Diethylamine Functionalized Soybean Oil." *J. Agric. Food Chem* (2005) 53, 9485-9490.
Blee, et al., "Soybean Epoxide Hydrolase: Identification of the Catalytic Residues and Probing of the Reaction Mechanism with Secondary Kinetic Isotope Effects." *Journal of Biological Chemistry* (2004) JBC Papers in Press, Published Dec. 13, 2004 as Manuscript M411366200.
Bournay, et al., "New Heterogeneous Process for Biodiesel Production: A way to Improve the Quality and the Value of the Crude Glycerin Produced by Biodiesel Plants." *Catalysis Today* (2005) 106, 190-192.
Corma, et al., "Chemical Routes for the Transformation of Biomass into Chemicals." *Chem. Rev.* (2007) 107, 2411-2502.
Di Serio, et al., "Transesterification of Soybean Oil to Biodiesel by Using Heterogeneous Basic Catalysts." *Ind. Eng. Chem. Res.* (2006) 45, 3009-3014.
Du, et al., "Catalytic Epoxidation of Methyl Linoleate." *JAOCS* (2004) 81.
Lanza, et al., eds., "Biofuels: Opportunity or Threat?" Environmental Grantmakers Association 2006.
Hazimah, et al., "Recovery of Glycerol and Diglycerol from Glycerol Pitch." *Journal of Oil Palm Research* (2003) 15(1), 1-5.
Kim, et al., "Transesterification of Vegetable Oil to Biodiesel Using Heterogeneous Base Catalyst." *Catalysis Today* (2004) 93, 95, 315-320.
Ma, et al., "Biodiesel Production: A Review." *Bioresource Technology* (1999) 70, 1-15.
Manzer, et al., "Biomass Derivatives: A Sustainable Source of Chemicals." NSF Workshop on Catalysis for Renewables Conversion, Washington D.C., Apr. 13-14, 2004.
Meher, et al., "Technical Aspects of Biodiesel Production by Transesterification: A Review." RSER 194 (2004) 18:41, 1-21.
Miller, et al., "Biorenewable Fuels and Chemicals via Reactive Distillation." Dept. Chemical Engineering and Materials Science presentation, Michigan University May 11, 2006.
Muturi, et al., "Epoxidized Vegetable Oils as Reactive Diluents I. Comparision of Vernonia, Epoxidized Soybean and Epoxidized Linseed Oils." *Progress in Organic Coatings* (1994) 25, 85-94.
Natl. Renewable Energy Laboratory, NREL/BR-510-39436, "From Biomass to Biofuels" (Aug. 2006).
Ono, et al., "Preparation, Surface-Active Properties and Acid Decomposition Profiles of a New 'Soap' Bearing a 1,3-Dioxolane Ring." *JAOCS* (1993) 70, 1.
Ono, et al., "Synthesis and Properties of Soap Types of Double-Chain Cleavable Surfactants Derived from Pyruvate." *J. Oleo Sci.* (2004) 53 (2), 89-95.
Rios, et al., "Textural and Chemical Characterization of Crystalline Ti-$SiO_2$ Catalysts Used in the Epoxidation of Fatty Esters." DYNA, Universidad Nacional de Colombia (2006) 73(148), 95-101. ISSN: 0012-7353.
Samuelsson, et al., "A Study of Fatty Acid Methyl Esters with Epoxy or Alkyne Functionalities." *JAOCS* (2001) 78(12), 1191-1196.
Sarnacke, S., "Soy Beans as Polymer Building Blocks." Omni Tech International, Ltd. presentation to United Soybean Board, Aug. 16, 2007.
Srivastava, et al., "Synthesis, Characterization and Curing Behaviour of Partial Esters of Cycloaliphatic Epoxy Resins." *Designed Monomers and Polymers* (2005) 8(4), 319-334.
Suppes, et al., "Calcium Carbonate Catalyzed Alcoholysis of Fats and Oils." *JAOCS* (2001) 78, 2, 139-146.
Thompson, et al., "Characterization of Crude Glycerol from Biodiesel Production from Multiple Feedstocks." *American Society of Agricultural and Biological Engineers* (2006) 22(2), 261-265.
Wedmid, et al., "Long-Chain Stereomeric 2-Alkyl-4-methoxycarbonyl-1,3-dioxolanes in Glycerol Acetal Synthesis." *J. Org. Chem.* (1977) 42(22), 3624-3626.

(Continued)

*Primary Examiner* — Taofiq Solola
(74) *Attorney, Agent, or Firm* — Cantor Colburn LLP

(57) ABSTRACT

Glyceryl ether compounds prepared by the reaction of glycerol and olefin epoxides are disclosed. The compounds are renewable biomass-based surfactants useful as detergents and emulsifiers in formulations for cleaning, laundry, personal care, cosmetics, and industrial uses.

3 Claims, 7 Drawing Sheets

OTHER PUBLICATIONS

International Preliminary Report on Patentability PCT/US2006/045191 issued May 27, 2008 with Written Opinion of the International Searching Authority completed Aug. 27, 2007, 6 pages.

Baskaran, S., et al., "An Efficient and Stereoselective Synthesis of (2R,2'S)-1-0-(2'-hydroxy-hexadecyl)glycerol and Its Oxo Analogs: Potential Antitumor Compounds from Shark Liver Oil", Tetrahedron, vol. 52, No. 18, pp. 6437-6452 (Apr. 29, 1996).

Blank, M.L, et al., The Biosynthesis of Plasmalogens from Labeled 0-Alkyl-glycerols in Ehrlich Ascites Cells, Biochimica and Biophysica Acta, vol. 210, pp. 442-427 (1970).

Blute, I., et al., Phase behaviour of alkyl glycerol ether sufactants, Tenside, Surfactants, Detergents, vol. 35, No. 3, pp. 207-212 (1998).

European Search Report for PCT/US2006/045191, mailed Jun. 9, 2011, 12 pages.

Karabina, E. And Borredon, M.E, "Synthesis of Hydroxyethers from Glycerol and Fatty Chains Epoxyalkanes in the Absence of Organic Solvent", Synthetic Communications, vol. 24, No. 21, pp. 3009-3019 (1994).

Muramatsu, T. And Schmid, H.H.O., "1-0-2'-Hydroxyalkyl and 1-0-2'-Ketoalkyl Glycerols", Chemistry and Physics of Lipids, vol. 9, No. 1, pp. 123-132 (Oct. 1, 1972).

Salager, J.L., Surfactants Types and Uses, FIRP Booklet#E300-A, Teaching Aid in Surfactant Science and Engineering, Universidad de Los Andes, Merida-Venezuela, Version #2, 50 pages, (2002).

\* cited by examiner

GLYCERYL ETHER COMPOUNDS AND THEIR USE

CROSS-REFERENCE TO RELATED APPLICATIONS

This application is a National Stage application under 35 U.S.C. §371 to International Application No. PCT/US2006/045191 having an International Filing Date of Nov. 22, 2006, which claims benefit under 35 U.S.C. §119(e) to U.S. Provisional Application No. 60/738,987 filed on Nov. 22, 2005, both of which are incorporated by reference in their entirety herewith.

TECHNICAL FIELD

The present disclosure relates to the preparation of compounds from glycerol and olefin epoxides.

BACKGROUND

Many surfactant compounds and soaps with various properties are known in the art. Of particular interest are non-ionic and ionic surfactant compounds that perform well in hard water containing elevated levels of alkali-earth metal salts. However, such surfactants are typically manufactured entirely, or in major part, from various expensive and often highly hazardous petrochemicals via complex chemical methods. Therefore, well-performing surfactants that utilize abundant, renewable, and inexpensive raw materials and simpler chemical synthesis methods are highly desired.

SUMMARY

Provided herein are a series of glyceryl ether compounds that have been found to be surfactant compounds having good solubilizing and emulsifying properties, including performance in water containing high concentrations of calcium and magnesium ions.

Glyceryl ether compounds can be prepared through the reaction of epoxidized normal alpha-olefin (NAO) compounds of formula (2), wherein $R^3$ can be a $C_6$-$C_{30}$ linear alkyl, or preferably, a

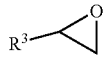
(2)

$C_6$-$C_{14}$ linear alkyl, and glycerol, or a protected glycerol of formula (3):

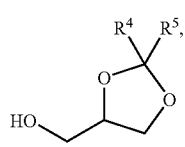
(3)

wherein $R^4$ and $R^5$ are independently selected from the group consisting of hydrogen; linear, branched, or cyclic alkyl; linear, branched, or cyclic alkenyl; aryl; and arylalkyl. The reaction can be performed in the presence of an acid or base catalyst. In certain embodiments, the reaction can be followed by deprotection of the ketal or acetal protecting group on the glyceryl moiety.

Examples of compounds prepared from glycerol, or a protected glycerol, and an epoxidized NAO can include the following formula:

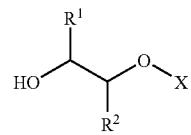

wherein one of $R^1$ and $R^2$ is hydrogen and the other is a $C_6$-$C_{30}$ linear alkyl; and X is selected from the group consisting of:

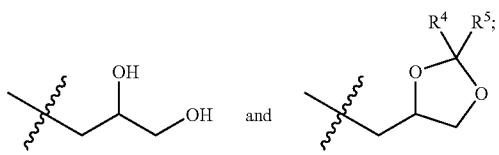

wherein $R^4$ and $R^5$ are as defined above.

In another embodiment, glyceryl ether compounds can be prepared from the reaction of glycerol, or a protected glycerol of formula (3), and an epoxidized triglyceride, or an epoxidized unsaturated fatty acid ester, wherein the fatty acid fragment has from 8 to 24 carbon atoms, and the alcohol fragment is a $C_1$-$C_{12}$ linear or branched monohydric alcohol. As above, the reaction can be performed in the presence of an acid or base catalyst. In certain embodiments, the reaction can be followed by deprotection of the ketal or acetal protecting group on the glyceryl moiety. In addition, the ester moiety can be converted to a free carboxyl group, a carboxylic salt, or an amide.

Examples of such compounds can include the formula:

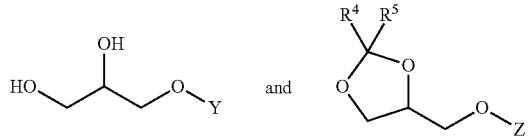

wherein one of A or B is hydrogen and the other is selected from the group consisting of carboxyl, carboxylate salt, and ester; m and n are independently integers from 0 to 20, and the value of the sum of m+n is in the range from 8 to 21; and Y and Z are independently selected from the group consisting of:

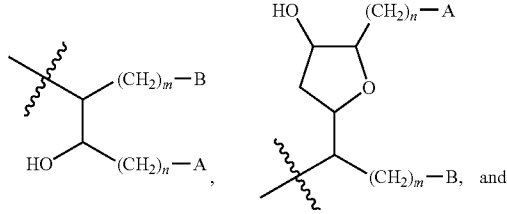

-continued
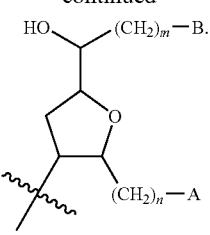
The reaction product can also include the formula:
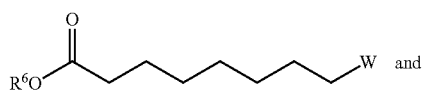 and
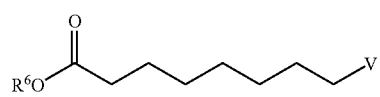
wherein $R^6$ is selected from hydrogen or a $C_1$-$C_{10}$ linear or branched alkyl; W is selected from the group consisting of:
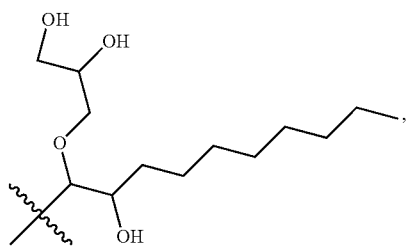
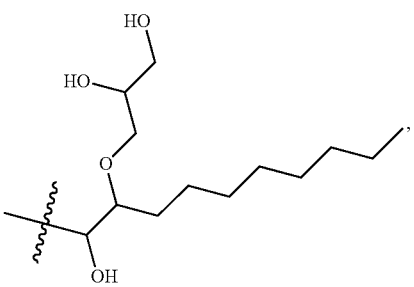
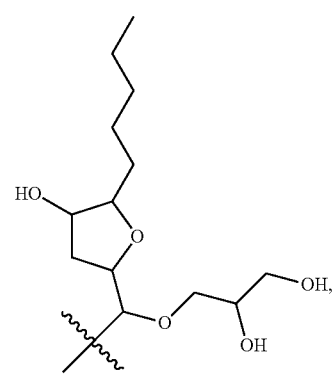
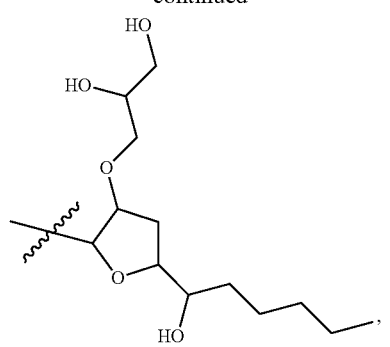
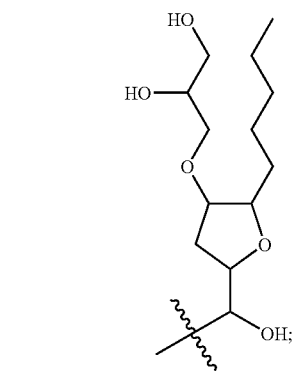
, and
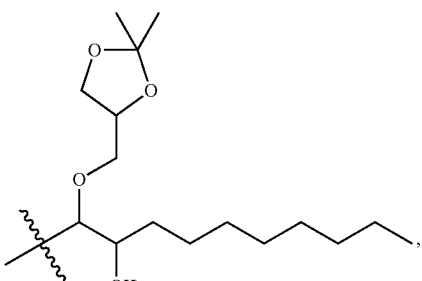
and V is selected from the group consisting of:
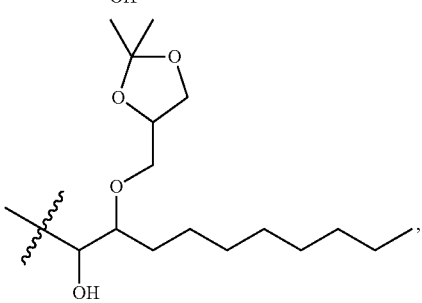

-continued

[chemical structures continued]

In some embodiments, the compounds above can be converted into their corresponding salt. In addition, the ester moiety in the above compounds can be converted to a free carboxyl group, a carboxylic salt, or an amide.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Referring now to the figures, which are exemplary embodiments.

DETAILED DESCRIPTION

Figure 1:
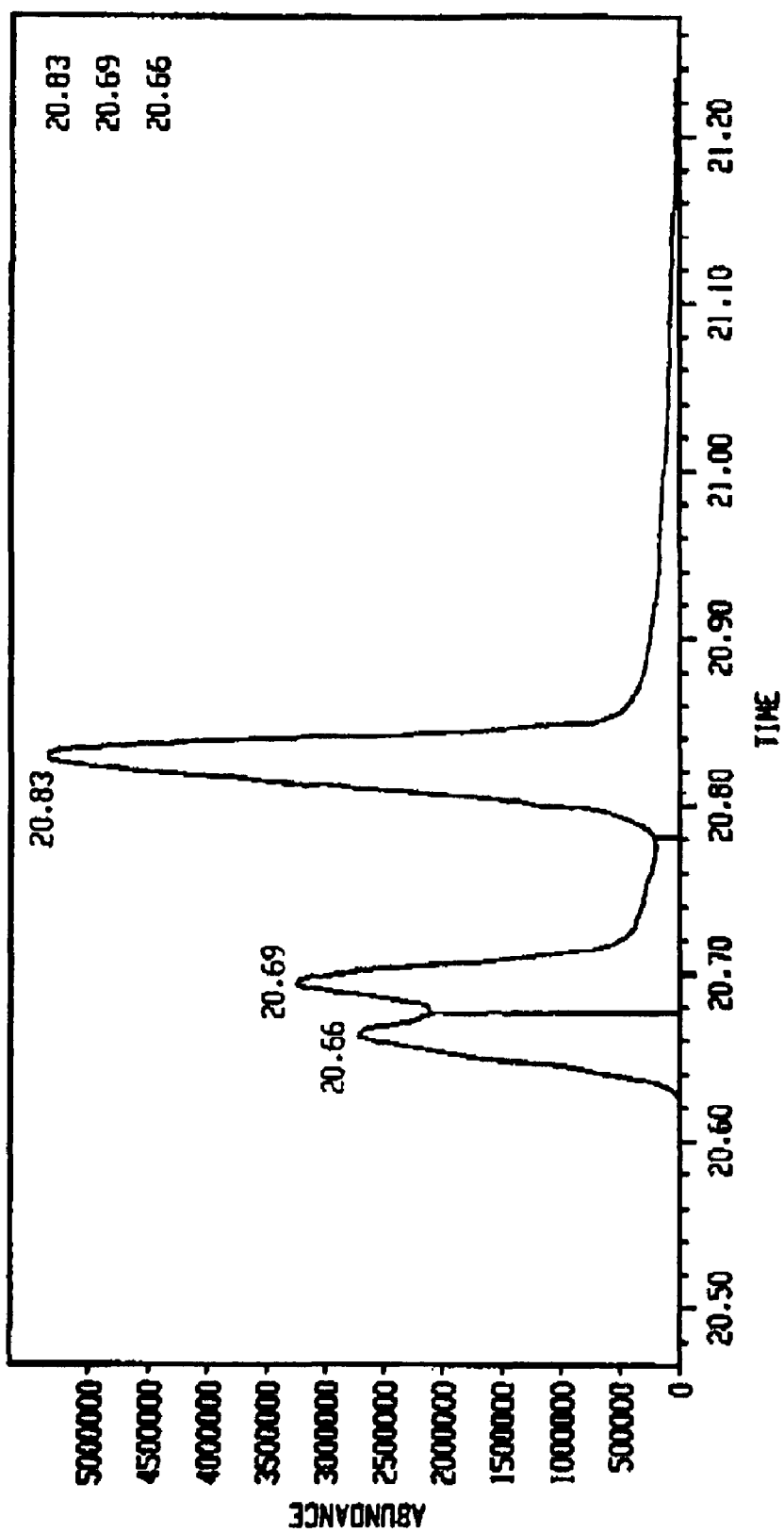
FIG. 1 is a total ion current chromatogram of the elution area for various isomeric compounds.

Provided herein are a series of glyceryl ether compounds that have been found to be surfactant compounds with good solubilizing and emulsifying properties, including performance in water containing a high concentration of calcium and magnesium ions. Glyceryl ether compounds are produced from glycerol, which is an abundant and inexpensive renewable material available as a by-product of the production of biodiesel fuels from triglycerides, and from relatively inexpensive epoxides of unsaturated compounds such normal alpha-olefins (NAO), or from epoxidized unsaturated fatty acid esters.

The first objective of the present disclosure is the provision of hydroxy alkyloxy-glyceryl ethers of formula (1):

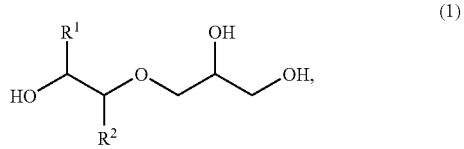

(1)

wherein one of $R^1$ or $R^2$ is hydrogen and the other is a $C_6$-$C_{30}$ linear alkyl, or preferably, a $C_6$-$C_{14}$ linear alkyl.

The compounds of formula (1) can be prepared from the 1,2-epoxides of NAO having formula (2):

(2)

wherein $R^3$ is a $C_6$-$C_{30}$ linear alkyl, and preferably, a $C_6$-$C_{14}$ linear alkyl.

The compounds of formula (2) are reacted with either glycerol or, preferably, with a protected form of glycerol, in the presence of a suitable catalyst. The protected form of glycerol can be a ketal or acetal of the glycerol of the formula (3):

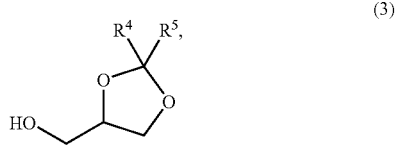

(3)

wherein $R^4$ and $R^5$ are each independently selected from hydrogen; linear, branched, or cyclic alkyl; linear, branched, or cyclic alkenyl; aryl; or aralkyl. Preferably, $R^4$ and $R^5$ are not both hydrogen.

Many ketals and acetals of formula (3), and methods for their preparation from glycerol, are known in the art. Typically, dioxolanes of formula (3) are prepared by reacting glycerol with a suitable linear, branched, or cyclic ketone or aldehyde in the presence of an acid catalyst, and under conditions allowing for removal of the water formed in the reaction. The removal of water is typically accomplished by a distillation if the boiling point of the ketone and aldehyde are both sufficiently above the boiling point of water, or by an azeotropic distillation with a suitable co-solvent. Dioxolanes of formula (3) can also be prepared by trans-ketalization or trans-acetalization of ketals or acetals of formula (4) with glycerol:

(4)

wherein $R^6$ and $R^7$ are independently selected from a $C_1$-$C_6$ linear or branched alkyl.

Suitable glyceryl ketals and acetals are compounds typically formed from glycerol and simple and inexpensive ketones and aldehydes that are readily available at industrial scale. Non-limiting examples of such ketones and aldehydes include acetone, 2-butanone, methyl isobutyl ketone, alkyl isopropyl ketones, cyclohexanone, cyclopentanone, isophorone, cycloheptanone, cyclododecanone, dihydroisophorone, menthone, camphor, and linear or branched aliphatic aldehydes, preferably, having 6 or more carbon atoms.

Acetals of glycerol and linear or branched aliphatic aldehydes commonly exist as an equilibrating mixture of 1,2-acetals (4-hydroxymethyl-1,3-dioxolanes) and 1,3-acetals (4-hydroxymethyl-1,3-dioxanes). Even in such mixtures, they are suitable for reaction with epoxides, but it is understood that 1,3-acetals of 2-glyceryl ether adducts may be formed. The presence of varying quantities of 1,3-acetals (or 1,3-ketals) in the starting materials does result in the formation of varying quantities of 1,3-ketals of 2-glyceryl ether products. This may diminish the usefulness of the resulting mixtures of compounds in the preparation of surface-active substances. It is preferred, therefore, that epoxides be reacted with 1,2-ketals of glycerol. In addition, acetals are more prone to the formation of peroxides and often have undesirable or annoying odors of trace free aldehydes.

When glyceryl ketals and acetals of formula (3) are reacted with an epoxide of formula (2), the resulting product is a mixture of stereoisomers having formula (5):

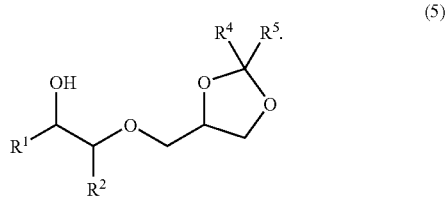

(5)

wherein one of $R^1$ or $R^2$ is hydrogen and the other is a $C_6$-$C_{30}$ linear alkyl, or preferably, a $C_6$-$C_{14}$ linear alkyl; and $R^4$ and $R^5$ are each independently selected from hydrogen; linear, branched, or cyclic alkyl; linear, branched, or cyclic alkenyl; aryl; or aralkyl.

The compound of formula (5) can be converted to the desired triol of formula (1), by treatment with sufficient amount of water or alkanol in the presence of an acid catalyst that is sufficient to cause hydrolysis or trans-ketalization but not elimination reactions. The deprotection step requires very mild conditions and may be expedited by heating the reaction mixture to the reflux temperature of the water or alkanol. When water is used, the ketone or aldehyde of formula $R^4$—(C=O)—$R^5$ is released, and can be separated and re-used in the process of making the protected glycerol of formula (3). When an alkanol is used, the ketal or acetal of formula (4) is released, which also can be separated and re-used in the synthesis of the compound of formula (3). The alkanol used in this reactions is preferably a linear or branched primary or secondary alkanol having from 1 to 6 carbon atoms.

The reaction between NAO epoxide of formula (2) and glycerol, or a glycerol derivative of formula (3), is typically carried out in the presence of a suitable catalyst. Catalysts for reacting epoxides of formula (2) with glycerol or with a compound of formula (3) can include various acids, and other catalysts known in the art. Such conditions are also generally applicable to the reactions of glycerol, or the compound of formula (3), with an epoxidized unsaturated fatty acid ester. Non-limiting examples of such catalysts include strong mineral acids, such as sulfuric, hydrochloric, hydrofluoroboric, hydrobromic acids, p-toluenesulfonic acid, camphorosulfonic acid, methanesulfonic acid, and the like. Various resins that contain protonated sulfonic acid groups are also useful as they can be easily recovered after completion of the reaction. Examples of suitable acids further include Lewis acids, for example, boron trifluoride and various complexes of $BF_3$, exemplified by $BF_3$ diethyl etherate. Other non-limiting examples of useful Lewis acids include halides of tin, titanium, aluminum, iron, silica, acidic alumina, titania, zirconia, various acidic clays, and mixed aluminum or magnesium oxides. Activated carbon derivatives comprising mineral, sulfonic, or Lewis acid derivatives can also be used.

The reaction can also be performed with a base catalyst. Various bases such as alkali metal alkoxides or hydroxides can be used as catalysts in the reaction between compound (2) and glycerol or compound (3). Useful solid catalysts are described in the United States Patent Application No. 2004/0077904 (Nagasawa, Atsushi, et al.; Apr. 22, 2004), and references cited therein.

The present disclosure is not limited to a specific catalyst or an amount of catalyst. One of ordinary skill in the art can practice many variations on the part of the catalyst composition and the amounts used. Elevated temperatures may be used to accelerate the reaction with less reactive catalysts, however, the temperature of the reaction mixture is not critical for succeeding in making a quantity of the glyceryl ether product, as even with less active catalysts the reaction still proceeds to yield the desired compounds. The amount and type of catalyst depends on the specific chemical composition of the epoxide and glycerol or glycerol derivative of formula (3), used in a reaction and can be readily established by one skilled in the art. It is understood that the use of different catalysts, such as different acids or bases, can and does result in the formation of the products of formula (1) or (5) with varying stereocompositon, because nucleophilic opening of epoxides in the presence of acids or in the presence of bases proceeds with different regioselectivity and stereoselectivity.

The reaction can be carried out in the presence of an optional co-solvent that is substantially inert under the reaction conditions and is often removed at the end of the reaction by distillation. Typically, it is desired to use a sufficient quantity of a co-solvent to minimize cross-linking of the epoxides via ether bond formation. Non-limiting examples of suitable co-solvents include saturated hydrocarbons, ethers, and polyethers. Any excess solvent remaining after completion of the reaction can be removed by distillation at normal or reduced pressure.

It has been found that compounds of formula (3) are very good solvents for NAO epoxides. The reaction between an epoxide and the glycerol derivative of formula (3) can also be conveniently performed in an excess of the latter compound, typically 2 to 20 times molar excess. When insufficient excess of the compound (3) is used, however, oligomeric adducts of compound (3) and two or more glycol ether fragments are formed as the major products. These compounds are also useful as surfactants, however, they are more expensive to manufacture due to the cost of the epoxide involved.

When free glycerol is reacted with NAO epoxides of formula (2), these reactants are generally immiscible in the absence of a suitable co-solvent. In such an embodiment, the reaction can be facilitated by vigorous stirring and by addition of one or more phase transfer catalysts, including surfactants of formula (1) or other surfactants/emulsifiers. Ether compounds that are alkylated oligomers of ethylene oxide are also useful as co-solvents and phase transfer reagents for this reaction. Reaction of unprotected glycerol with NAO epoxides of formula (2) typically results in the formation of higher quantities of various byproducts, due to epoxide oligomerization and due to epoxide opening reactions that involve more than one hydroxyl group of the same glycerol molecule.

The compounds of formula (1) can be obtained and used in a neat (solventless) form, or as a concentrated solution in an aqueous solvent, including pure water and water-solvent mixtures.

Neat compositions of formula (1) are most conveniently obtained by deprotecting a compound of formula (5) in the presence of excess alkanol as described above, followed by removal of the alkanol and compound (4) by distillation. It is also advantageous to remove any other volatile odoriferous impurities that may be present in the industrial grade NAO epoxides (such as traces of hydrocarbons, alkanals and alkanones).

The compounds of formula (1) in neat form, when obtained from NAO epoxides having from 8 to 16 carbon atoms, are paste-like solids or viscous liquids, while compounds from NAO epoxides having 18 or more carbon atoms are waxy solids. The compounds from NAO epoxides having from 8 to 18 carbon atoms have very good solubility in water, water-alcohol, and water-propylene glycol mixtures, giving characteristic opalescent smectic appearance to such solutions. The compounds from NAO epoxides having 18 carbon atoms or more, on the other hand, are somewhat less soluble and may precipitate in cold water. Good solubility properties are advantageous for using compounds of formula (1) in various formulations where surfactant or emulsifying properties are desired. The compounds of formula (1) are stable in cold and hot aqueous solutions over a broad range of pH values (i.e, from pH 2 to pH 13). Compounds of formula (1) are non-ionic surfactants, and their surfactant and emulsifying or micelle-forming properties are not substantially affected by the presence of alkali-earth metal ions in the solution.

Compounds of formula (1) can be used in a manner substantially similar to that of other non-ionic surfactants known in the art. Compounds of formula (1) can thus be used alone or in various combinations with other surfactants, solvents, glycols and polyols, fragrances, colors, biologically-active and inert additives, enzymes, inorganic salts such as chloride and sulfate salts of alkali metals, fabric wetting agents, antiseptics, and bleaching agents. The compounds can used in cleaning, dishwashing, laundry, cosmetic and personal care products, degreasing preparations, and the like. Effective concentrations for use of compounds of formula (1) depend on the intended use of the formulation and can be easily established empirically by one of ordinary skills in the art. The effective concentrations for compounds of formula (1) can typically range from 0.001% to 100% of the formulated product.

In another embodiment, surfactant compounds can be prepared from epoxides of unsaturated fatty acid esters. These compounds are prepared in the manner similar to the above-described methods for making compounds of formula (1) from the NAO epoxides of formula (2).

The following terms apply:

Unsaturated fatty acids mean linear monocarboxylic acids having from 10 to 24 carbon atoms and at least one double bond. The double bonds can be in any positions, conjugated with each other or non-conjugated, but not in allenic arrangements, and any of the double bonds can be independently cis or trans. Preferably, fatty acids have one or two double bonds, and more preferably, only one double bond.

Esters of fatty acids mean esters of the above-described fatty acids with monohydric alcohols.

Monohydric alcohols are linear or branched primary or secondary alkanols having from 1 to 12 carbon atoms. Preferred examples of alkanols are methanol, ethanol, propanol, isopropanol, butanol, secondary butanol, isobutanol, isoamyl alcohol, and 2-ethylhexanol.

It is understood that in industrial practice, where mixed fatty acid compositions are used, not all of the fatty acid esters present in the starting material can be unsaturated and some fully saturated fatty acid groups can be present in the ester mixtures. In fact, it is cost-advantageous to use mixtures of unsaturated and saturated fatty acid esters such as triglycerides of typical vegetable oils (e.g., soybean oil, linseed oil, canola oil, safflower oil, sunflower oil, corn oil, castor oil, their blends and the like). It is preferred, however, that the mixed fatty acid esters contain predominantly unsaturated fatty acid esters. It is also preferred that a fatty acid ester with a high content of mono-unsaturated fatty acid ester is used, such as the compositions found in high oleic canola oil. Esters of 10-undecylenic acid are also preferred. Another preferred starting material is a mixture of methyl esters of fatty acids derived by trans-esterification of vegetable oils (e.g. of soybean oil, canola oil and other unsaturated triglycerides commonly used in the industrial production of biodiesel fuel).

Various unsaturated fatty acid esters can be optionally blended, mixed, partially hydrogenated, or otherwise isomerized to change the position or stereochemistry of the double bonds. It is particularly advantageous to isomerize natural mono-unsaturated fatty acid esters with the purpose of shifting the position of the double bond to a position in proximity of the carboxyl group, e.g., the 2,3-position to yield alk-2-enoic esters. Similarly, it is preferred that natural di-unsaturated fatty acid esters be isomerized to alka-2,4-dienoic esters. Such isomerization products are favored during catalytic isomerization of esters in the presence of an acid or a Lewis acid, or in the presence of a metal catalyst. Metal catalysts ordinarily used in the hydrogenation of alkenes can include palladium, ruthenium, iridium, copper chromite, nickel salts, and the like.

Epoxidized unsaturated fatty acid ester means that at least one of the double bonds of the unsaturated fatty acid ester is oxidized to an epoxy group. Such oxidations are well known in the art and can be readily accomplished at an industrial scale, e.g., by using hydrogen peroxide and a carboxylic acid (e.g. formate or acetate), or by the halohydrin method. It is preferred, however, that epoxidation of at least one of the double bonds present in the unsaturated fatty acid ester is accomplished. It is understood that in practice, epoxidized fatty acid esters may contain various quantities of by-products arising from hydrolysis or rearrangement of epoxides and from cross-linking of the fatty acid chains. Use of epoxidized fatty acid esters containing small quantities of epoxidation by-products and epoxide decomposition by-products is fully within the scope of the present disclosure.

Glyceryl ethers derived from epoxides of mono-unsaturated fatty acid esters can have the formula (6):

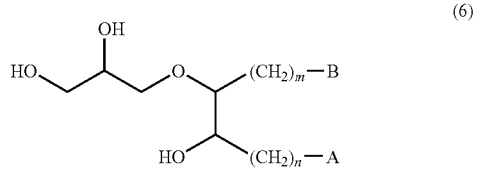

(6)

wherein one of A or B is hydrogen and the other is selected from the group consisting of carboxyl, carboxylate salt, and ester; and n and m are integers each having values from 0 to 20, and the value of the sum of m+n is in the range from 8 to 21.

When bis-epoxides or tris-epoxides of unsaturated fatty acid esters having epoxy groups positioned in close proximity to one another are used, an intra-molecular epoxide opening reaction can take place, resulting in the formation of one or more ether bonds connecting two carbon atoms of the continuous fatty acid carbon chain. Typically, such ether bonds result in the formation of a tetrahydrofuran (major) and tetrahydropyran (minor) rings. Complex mixtures of stereoisomers of oxygenated derivatives of fatty acid esters are formed. For example, representative isomers of the such surfactant products from a bis-epoxide from a di-unsaturated fatty acid having two double bonds separated by a methylene group can have formulae (7a) and (7b):

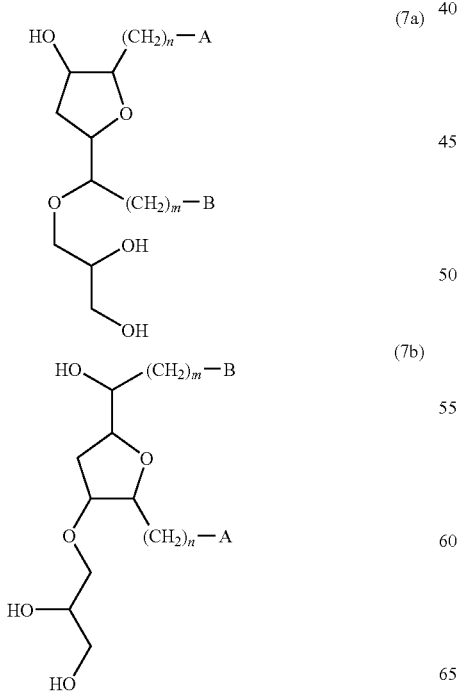

wherein A, B, m, and n are as defined above.

Compounds of formula (7a) and (7b) are typically formed as mixtures that can also include other adducts, such as di(glyceryl)ether adducts resulting from the opening of each of the epoxy groups with a different glycerol fragment, thereby resulting in oxygenated fatty acid derivatives comprising two hydroxyl groups and two pendant glyceryl ether groups.

Preferably, the glyceryl ether adducts of epoxidized fatty acid esters are formed by the reaction of a protected glycerol of formula (3), followed by the removal of any excess compound of formula (3) by distillation, and by deprotection of the glyceryl ether ketal/acetal moiety.

Alternatively, the glyceryl ether adducts of epoxidized fatty acid esters can be prepared by treating epoxidized triglycerides with the compound of formula (3) in the presence of catalyst substantially similar to the catalysts described. In such an embodiment, triglyceride polyol compounds are formed. These compounds have free secondary hydroxyl groups and glyceryl ether pendant groups attached to the fatty acid chains. Optionally, ether bonds may also be present in such adducts and the ether bonds can connect two carbon atoms of one fatty acid chain (thereby forming a tetrahydrofuran or a terahydropyran ring) or two different fatty acid chains.

Such adducts of glycerol or of a ketal/acetal protected glycerol with an epoxidized triglycerides are typically prepared from epoxidized soybean oil, linseed oil and the like. These adducts have been found to be useful in the production of compounds of formula (6), (7a), and (7b), as well as their corresponding ketals/acetals of formulae (8), (9a) and (9b):

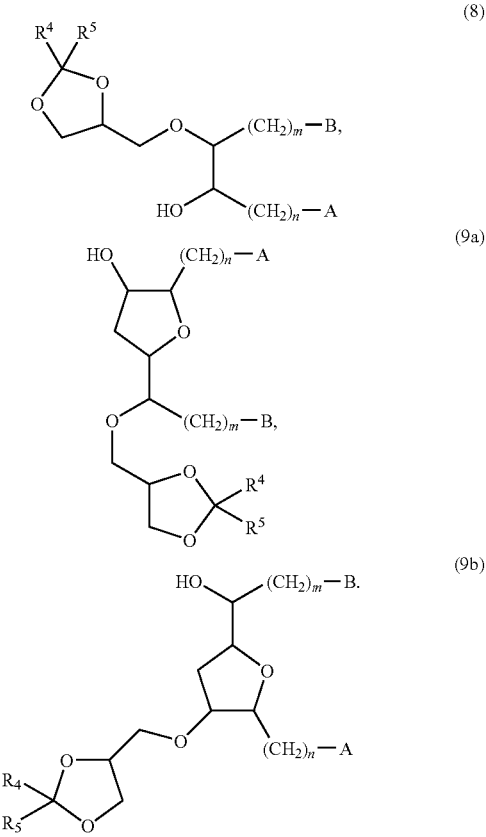

The conversion of the triglyceride adducts to the compounds (8), (9a) and (9b) is most readily accomplished by a trans-esterification reaction with a monohydric alkanol in the presence of catalytic amount of base. Non-limiting examples of suitable bases are hydroxides of alkali or alkali-earth metals or alkoxides of alkali metals and alkanols. Deprotection of ketal/acetal groups of the compounds (8), (9a), and (9b) is readily accomplished by using an alkanol in the presence of an acid catalyst, thereby resulting in the formation of the compounds (6), (7a), and (7b), respectively.

The deprotection of the ketal groups and trans-esterification of triglyceride ester bonds with a monohydric alcohol can also be combined and carried out in the presence of a catalytic amount of an alkanol and an acid. Typically, an excess of monohydric alkanol is used, and when the reaction is substantially complete, excess alkanol and ketal (4) are removed by distillation. Any glycerol formed in this reaction can also be separated and re-used in the synthesis of glyceryl ether compounds as described herein.

The resulting ether adducts of glycerol and the hydroxylated fatty acid esters (as exemplified by compounds of formula (6), (7a), (7b)) are useful non-ionic surfactants that can be used in various formulations in a manner substantially similar to the non-ionic surfactants of formula (1) disclosed above.

The carboxyl group in the ether adducts of glycerol and the hydroxylated fatty acid esters can optionally be saponified to furnish a salt (typically, alkali, alkali-earth, ammonium, or an amine salt). The carboxyl group can also be protonated. Furthermore, the carboxyl group can be amidated with a primary or a secondary alkylamine or an aminoalcohol. Such secondary derivatives resulting from the chemical modifications at the carboxyl group are useful ionic surfactants that work well in hard water. Similarly to compounds of formula (1), (6), (7a), and (7b), these compounds can be used to formulate various surfactant and emulsifier preparations according to methods known in the art.

EXAMPLES

Example 1

5 g of decene-1,2-oxide of 94% purity was dissolved in 15 ml of solketal and stirred by means of magnetic stirring at room temperature (25° C.). Boron trifluoride diethyl etherate (0.05 ml) was added by means of a syringe, and the reaction mixture was stirred for 20 min. During this time, an exothermic reaction was observed and the temperature was allowed to rise to about 55° C. 0.5 g of ammonium fluoride was added and the suspension was stirred for another 2 hrs. The resulting mixture was filtered, and unreacted solketal was removed under reduced pressure. The resulting colorless liquid (7.8 g) was analyzed by gas chromatography-mass spectrometry (GC-MS) and was found to contain approximately 85% of a mixture of stereoisomers of ketal compounds of formulae (10a) and (10b):

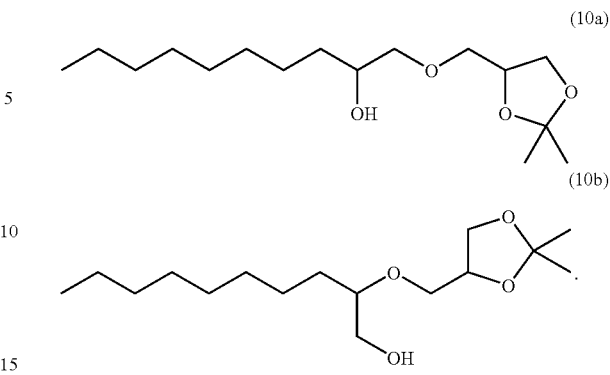

These compounds were detected as a mixture that manifested as three partially resolved peaks on the GC chromatogram as shown in FIG. 1. The three peaks in the chromatogram correspond to the partially resolved mixture of the isomeric compounds of formulae (10a) and (10b).

Small amounts of the stereoisomers of the compound of formula (10c) were also present in the isolated reaction mixture:

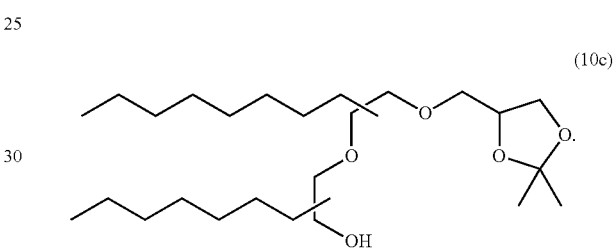

Figure 2:
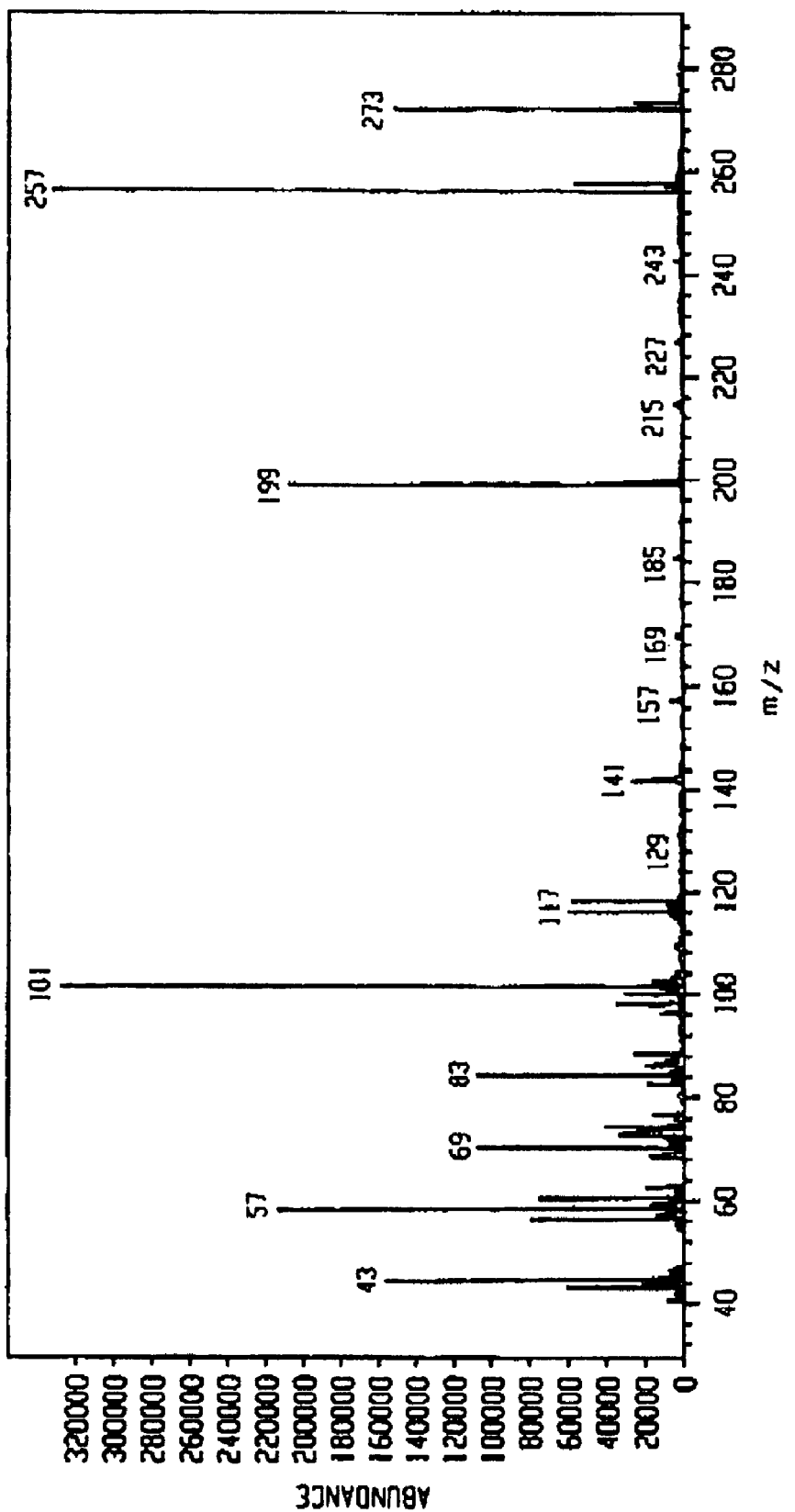
FIG. 2 is a mass spectrum corresponding to the first peak of the chromatogram shown in FIG. 1.
Figure 3:
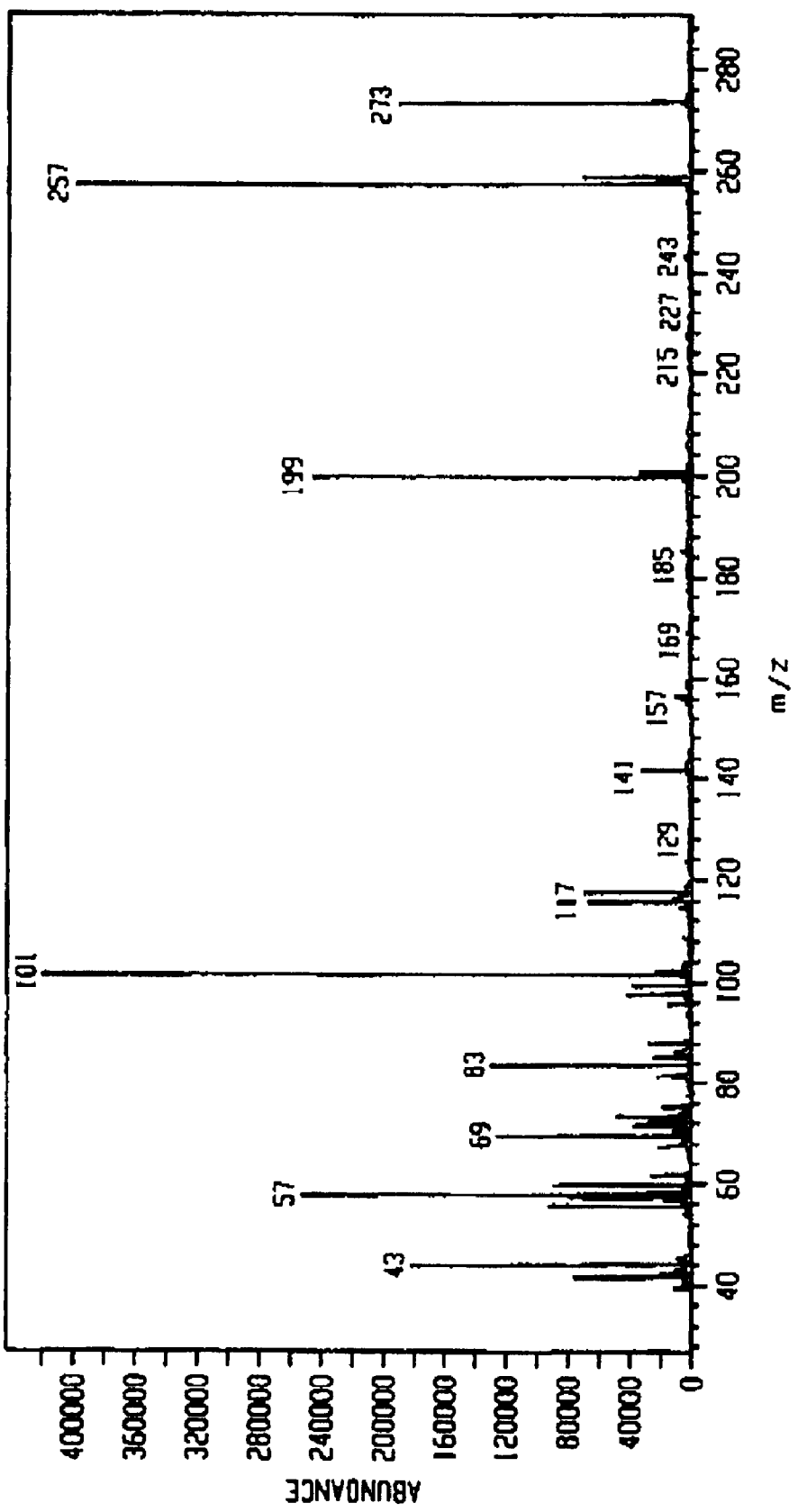
FIG. 3 is a mass spectrum corresponding to the second peak of the chromatogram shown in FIG. 1.
Figure 4:
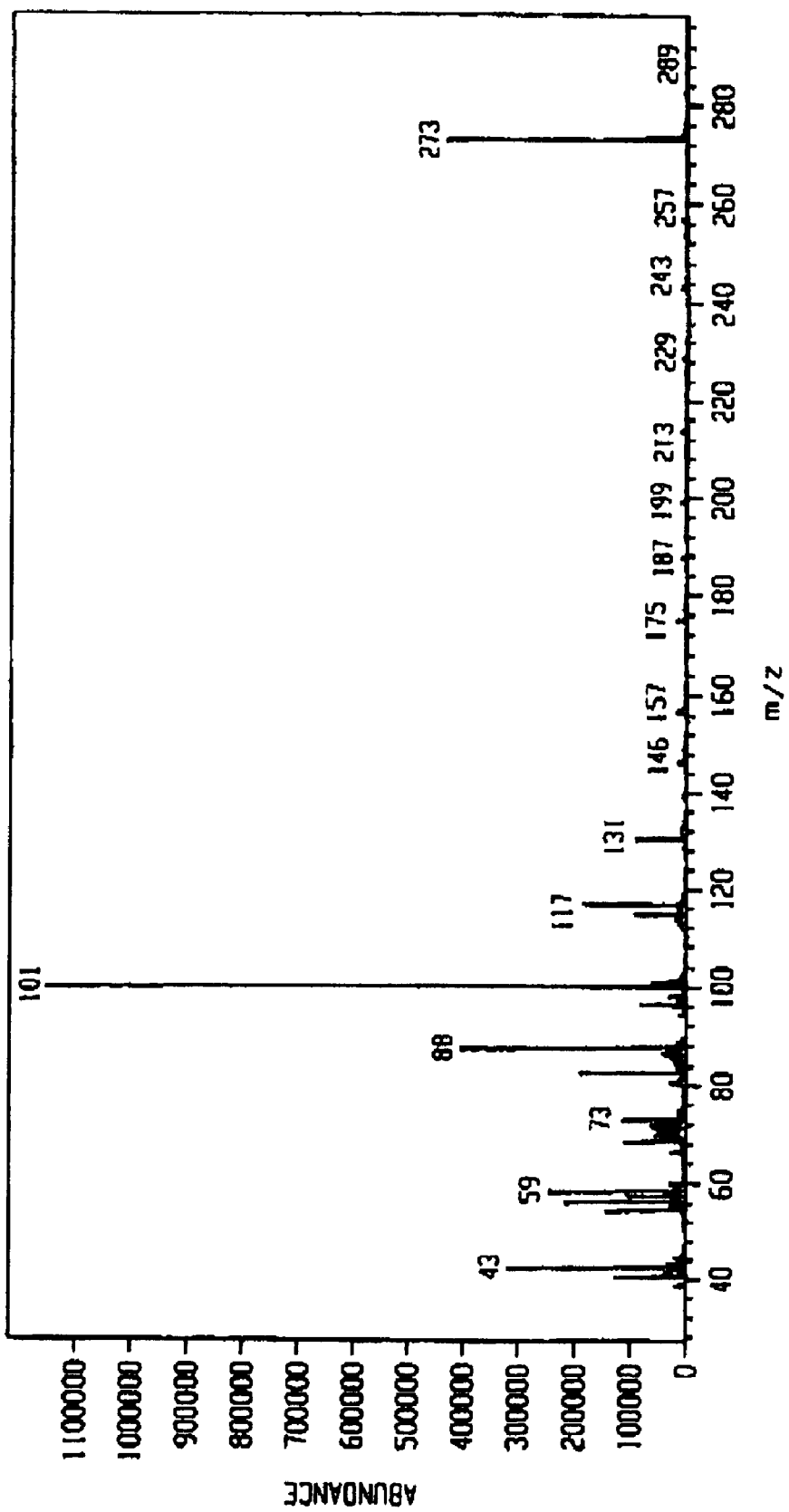
FIG. 4 spectrum corresponding to the third peak of the chromatogram shown in FIG. 1.

The isomers of compound (10a) and (10b) had representative mass-spectra shown in FIG. 2. FIG. 2 is a mass spectrum corresponding to the first peak of the chromatogram shown in FIG. 1. FIG. 3 is a mass spectrum corresponding to the second peak of the chromatogram shown in FIG. 1, and FIG. 4 is a mass spectrum corresponding to the third peak of the chromatogram shown in FIG. 1.

Example 2

The reaction was carried out according to Example 1, except 5 g of octadecene-1,2-oxide of 85% purity was used, and the reaction was carried out at 60° C. to facilitate dissolution of the starting material in solketal. The resulting waxy and oily Mixture of compounds (5.7 g) was analyzed by GC-MS and was found to contain approximately 75% of mixed isomeric compounds having formula (11a) and (11b):

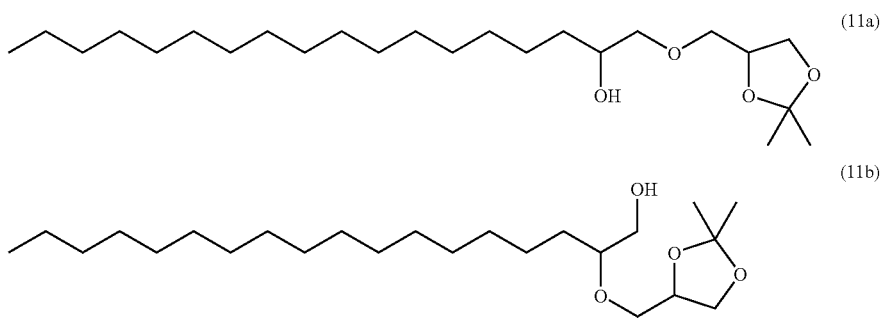

Figure 5:
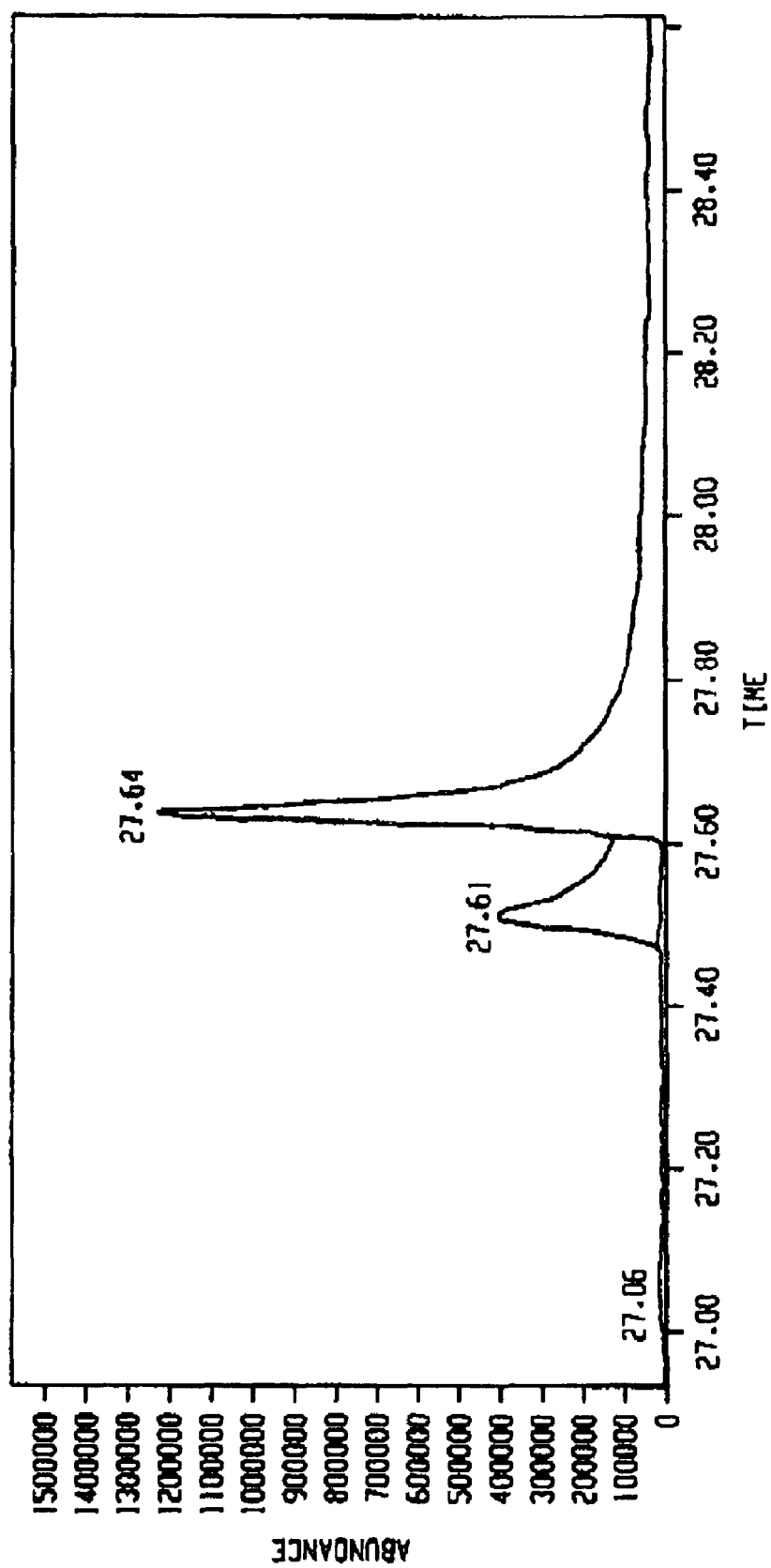
FIG. 5 is a total ion current chromatogram of the elution area for various isomeric compounds.
Figure 6:
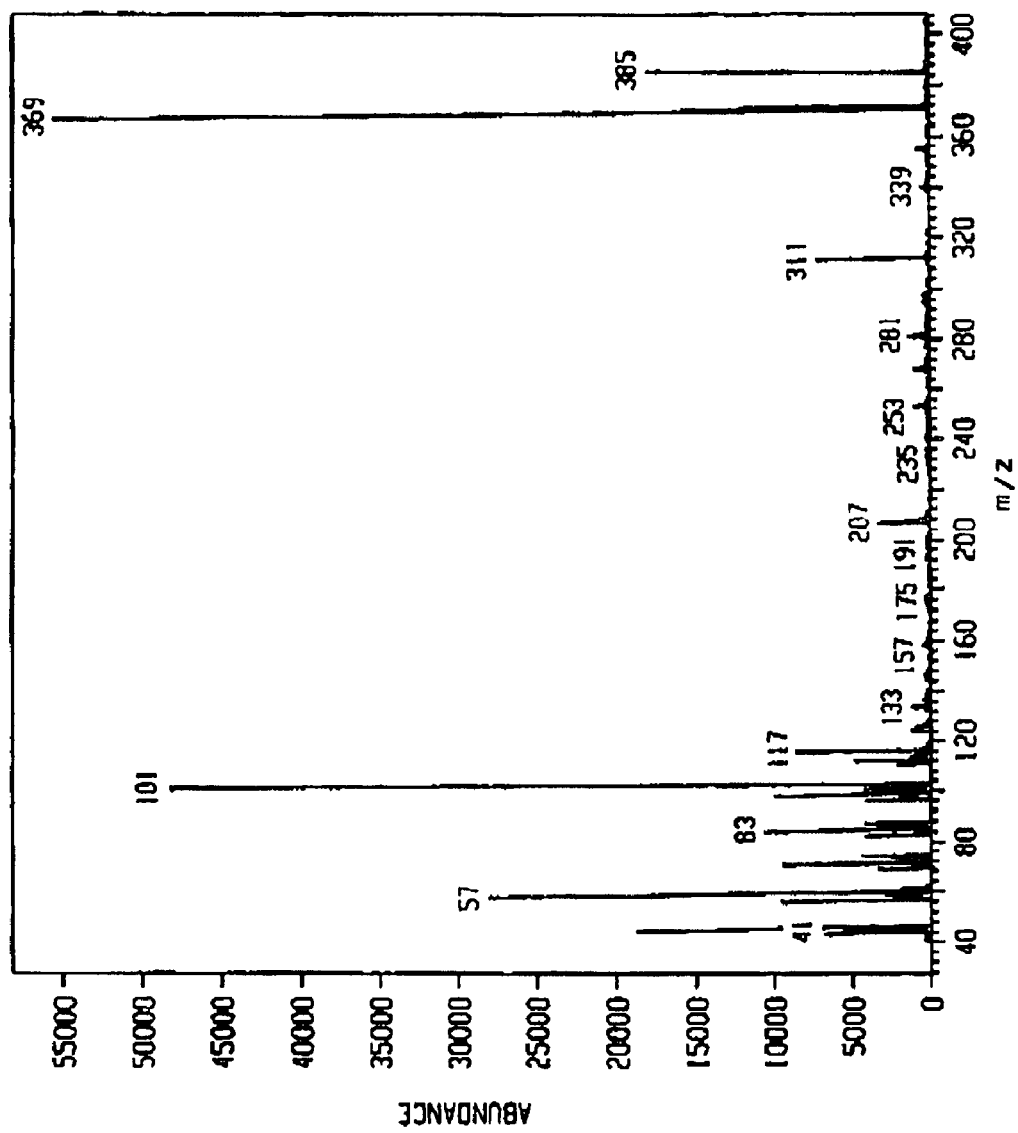
FIG. 6 is a mass spectrum corresponding to the first peak of the chromatogram shown in FIG. 5.
Figure 7:
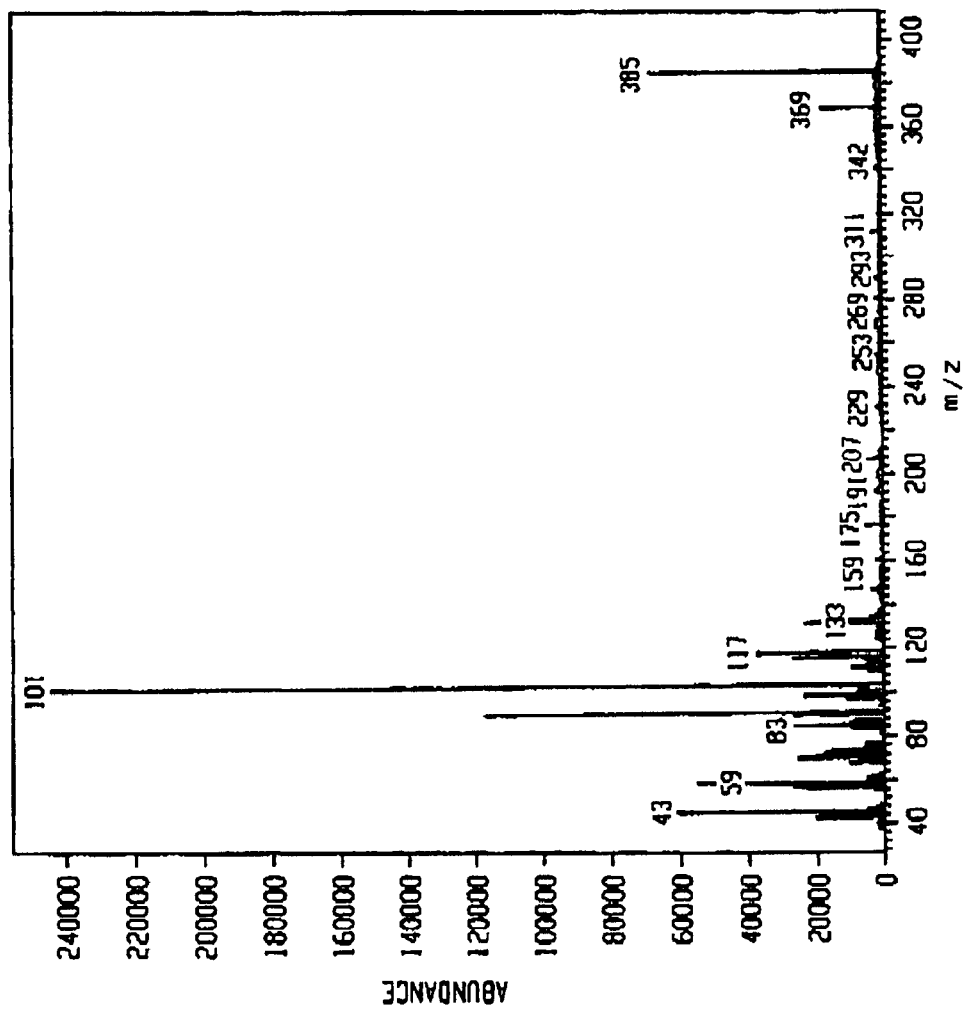
FIG. 7 is a mass spectrum corresponding to the second peak of the chromatogram shown in FIG. 1.

FIG. 5 shows a partial TIC chromatogram of the elution area where isomeric compounds (11a) and (11b) elute. FIG. 6 is a mass spectrum corresponding to one peak of the chromatogram shown in FIG. 5, and FIG. 7 is a mass spectrum corresponding to other peak of the chromatogram shown in FIG. 5.

Example 3

1 g of reaction product obtained in Example 1, 5 g of water, and 0.01 g of sulfuric acid were combined by means of continuous magnetic stirring and heated for 2 hours at 90-95° C. The reaction mixture was then cooled to room temperature, neutralized by means of addition of calcium carbonate (0.1 g), and filtered. The reaction mixture was a characteristic opalescent smectic solution. Upon evaporation of water under reduced pressure, 0.6 g of viscous oily-waxy opalescent residue with a pearl-like appearance was obtained. The resulting compound contained predominantly stereoisomers of compounds 12a and 12b:

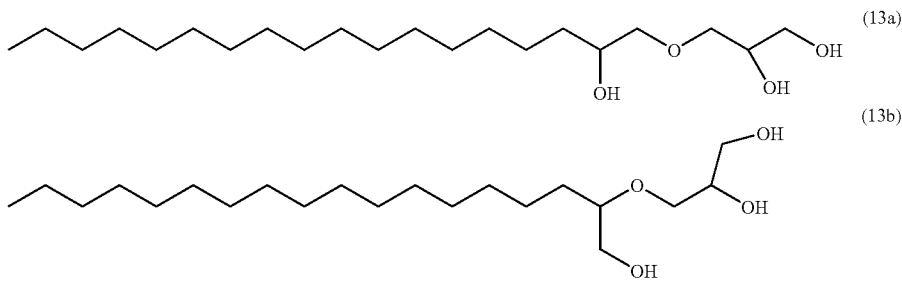

The aqueous solutions of the mixture of isomers of compounds (12a) and (12b) were able to form stable emulsions of hexane in water at (1:1 vol) when the concentrations of compounds (12a) and (12b) were in excess of 0.2%. The emulsifying properties of compounds (12a) and (12b) were not disrupted by the addition of 0.2% calcium chloride or magnesium chloride.

Examples 4-5

1 g of the reaction product obtained in Example 1, 5 g of methanol (Example 4) or n-butanol (Example 5) and 0.05 g of p-toluene sulfonic acid were dissolved and stirred by means of magnetic stirring for 48 hours at room temperature. The resulting solution was neutralized by the addition of 0.1 g of calcium carbonate, stirred for 1 hour and filtered. The excess alcohol and small quantities of 2,2-dimethoxypropane (Example 4) or 2,2-dibutoxypropane (Example 5) were removed under reduced pressure, affording 0.55 and 0.58 g, respectively, of a material containing compounds of formula (12a) and (12b); identical in all respects to the compounds prepared in Example 3.

Example 6

The reaction was carried out according to Example 3, except that the starting material prepared in Example 2 was used. The resulting waxy solid (3.9 g, m.p. 42-46° C.) contained predominantly compounds of formula (13a) and (13b):

Aqueous solutions of the mixture of isomers of compounds (13a) and (13b) were able to support stability of emulsions of water in hexane. The emulsifying properties of compounds (13a) and (13b) were not substantially disrupted by the addition of 0.2% calcium chloride or magnesium chloride.

Examples 7-8

The synthesis was carried out according to Examples 4-5, except the starting material used was prepared according to Example 2. The isolated mixture of compounds (13a) and (13b) was in all respects identical to that obtained in Example 6.

Example 9

10 g of decene-1,2-oxide and 25 ml of glycerol were vigorously stirred at room temperature. Boron trifluoride diethyl etherate was added by means of a syringe in 10 minute intervals (3 portions of 0.2 ml each), and the reaction mixture was stirred for an additional hour. The resulting mixture was then left standing and excess glycerol was separated by means of a reparatory funnel. The upper phase liquid contained a mixture of adducts comprising compounds of formula (11a), (11b), (11c), and the isomers of a bis-hydroxydecyl glyceryl ether. The resulting mixture had a similar surfactant and emulsifying capability to the material prepared in Example 2.

Example 10

The reaction was carried out according to the conditions of Example 1, except the starting material was a fully epoxidized mixture of fatty acid methyl esters obtained by methanolic trans-esterification of epoxidized soybean oil (Vicoflex® brand, Arkema), and the reaction with solketal was carried out at 60° C. The resulting mixture of products (6.4 g) was analyzed by GC-MS and was found to contain several stereoisomers of solketal ether adducts among which were compounds of formulae (14a), (14b), (15a), (15b), (15c), and (15d), wherein $R^6$=methyl:

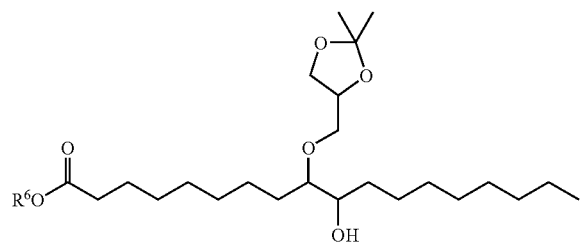
(14a)

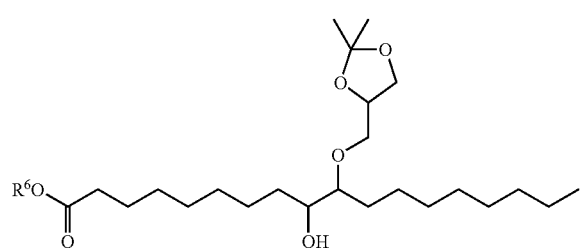
(14b)

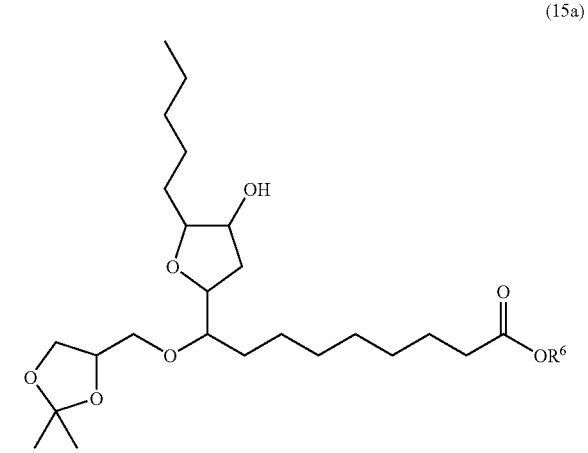
(15a)

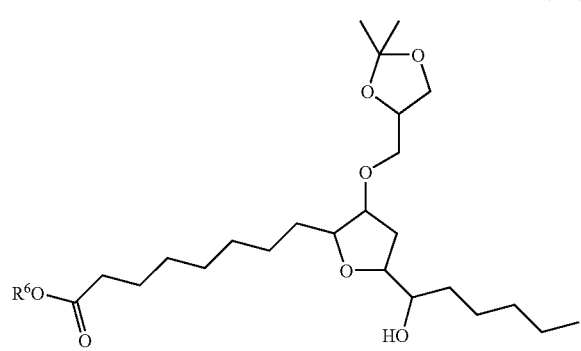
(15b)

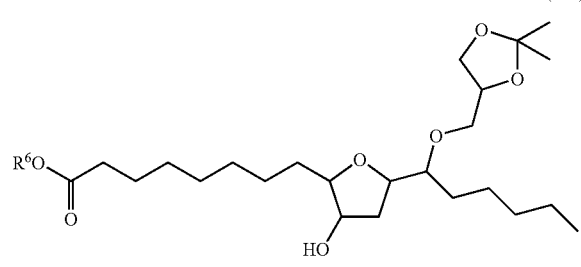
(15c)

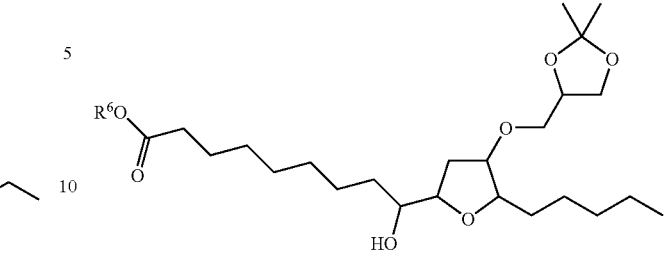
(15d)

Methyl esters of hexadecanoic acid and octadecanoic acid were also present. Small quantities of other unidentified modified fatty acid ester products, as well as products arising from the rearrangement of the epoxides on the carbonyls, were also observed.

Example 11

3 g of the material obtained in Example 10 was heated to 100° C. at 0.5 mm vacuum for 24 hours with stirring to reduce the content of methyl ester of hexadecanoic acid to a value less than approximately 1% by weight of the starting material (approximately 10% weight loss). The resulting oil was dissolved in 20 ml of methanol and refluxed with 0.2 g of tosic acid for 24 hours. The reaction mixture was then neutralized with 0.5 g of calcium carbonate, filtered, and the methanol and 2,2-dimethoxypropane were removed under reduced pressure to give 1.9 g of a waxy low-melting solid comprising a mixture of glyceryl ether adducts of methyl esters of modified fatty acids represented by formulae (16a), (16b), (17a), (17b), (17c), (17d):

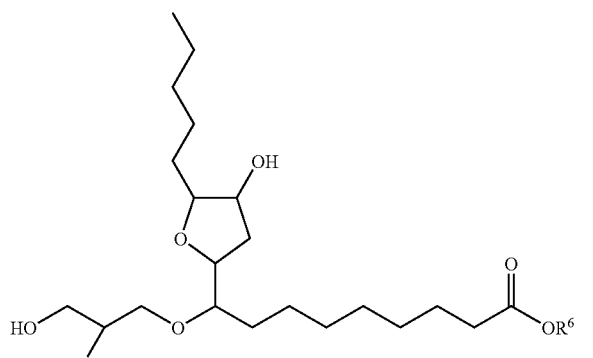

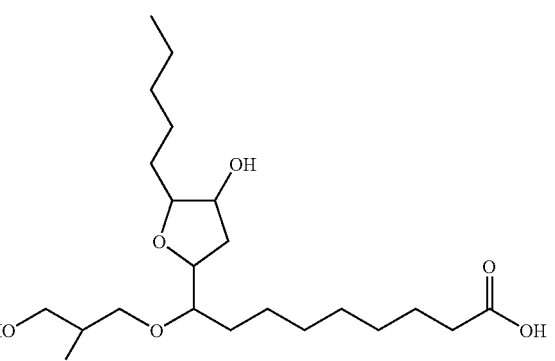

wherein R⁶ is methyl.

The waxy product was then saponified in 20 ml of water at 60° C., by stirring and titrating dropwise with 1 N aqueous sodium hydroxide to maintain pH 8-10. The resulting soapy solution contained sodium salts of carboxylic acid compounds of formulae (18a), (18b), (19a), (19b), (19c), and (19d):

The mixture of sodium salts had good surfactant and emulsifying properties that were not adversely affected in the presence of 0.1% calcium chloride.

Example 12

5 g of epoxidized soybean oil (Vicoflex® 7170 brand, Arkema) was dissolved in 20 ml of solketal. The reaction mixture was heated and stirred at 60° C., and 0.2 g of BF$_3$ diethyl etherate was added over 15 min (4 portions of 0.05 ml each). The reaction mixture was stirred for 1 hour and then cooled to the room temperature. The catalyst was neutralized by stirring with 0.5 g of ammonium fluoride for 1 hour and the whole was filtered. Excess solketal was removed by distillation under reduced pressure to give 5.7 g of a transparent, free flowing, practically colorless, very viscous liquid that comprised a mixed ether polyol adduct of epoxidized fatty acid triglyceride and 1,2-isopropylidene glycerol.

1 g of the resulting material was dissolved in 10 g of methanol and refluxed for 24 hours in the presence of 0.05 g of p-toluenesulfonic acid. The solution was then neutralized by the addition of 0.2 g of calcium carbonate, stirred for 2 hrs and filtered. Methanol was removed under reduced pressure and about 0.8 g of a waxy solid was obtained. The waxy solid was dissolved in 10 ml of water and saponified in a manner described in Example 11. The resulting soapy solution contained sodium salts of a mixture of compounds that had a very similar composition and surfactant properties to the material obtained in Example 11.

Example 13

The synthesis was carried out as in Example 1, except that 25 g of 1,2-glyceryl ketal of menthone was used in place of solketal, and the reaction was carried out at 60° C. After removal of any excess 1,2-glyceryl ketal of menthone, the resulting oil was treated by stirring with methanol (40 ml) in the presence of 0.2 g of p-toluene sulfonic acid at room temperature for 4 days. The reaction was neutralized by stirring with 2 g of calcium carbonate for 24 hours and then filtered. The filtrate was evaporated under reduced pressure to distill out any methanol, menthone dimethyl ketal, and menthone present. The surfactant properties of the resulting mixture of products were substantially similar to those obtained in Example 3.

Example 14

The synthesis was carried out as in Example 13, except that 1,2-glyceryl ketal of camphor was used.

Examples 15-17

The synthesis was carried out according to Example 1, except that in place of decene-1,2-oxide, 5 g of one of the following epoxides was used (each was 90-94% pure):
 (Example 15) dodecene-1,2-oxide,
 (Example 16) tetradecene-1,2-oxide,
 (Example 17) hexadecane-1,2-oxide.

The resulting product mixtures were deprotected on the part of removal of the acetonide groups according to the conditions of Example 3. The resulting hydroxyalkyl glyceryl ether adduct mixtures were similar in their surfactant and emulsion properties to those obtained in Example 3.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A compound having the formula:

$$R^6O-C(=O)-(CH_2)_n-V$$

wherein:
R$^6$ is selected from hydrogen or a C$_1$-C$_{10}$ linear or branched alkyl; and V is selected from the group consisting of:

[structure 1: acetonide-CH$_2$-O-CH(attachment)-CH(OH)-(CH$_2$)$_6$-CH$_3$]

[structure 2: acetonide-CH$_2$-O-CH(attachment)-CH(OH)-(CH$_2$)$_{10}$-CH$_3$], and

[structure 3: tetrahydrofuran ring with HO, pentyl substituent, and O-CH$_2$-acetonide group]

2. A method for preparing a compound of claim 1, the method comprising:
 a) providing a glycerol or a compound of the formula:

[structure: 1,3-dioxolane with R$^4$, R$^5$ at 2-position and HOCH$_2$- at 4-position]

wherein:
R$^4$ and R$^5$ are independently selected from the group consisting of hydrogen; linear, branched, or cyclic alkyl; linear, branched, or cyclic alkenyl; aryl; and arylalkyl;
 b) providing a compound selected from the group consisting of: an epoxidized triglyceride, and an epoxidized unsaturated fatty acid ester, wherein the fatty acid fragment has from 8 to 24 carbon atoms, and the alcohol fragment is a fragment of a C$_1$-C$_{12}$ linear or branched monohydric alcohol; and c) effecting a reaction between the compounds of a) and b) in the presence of an acid or base catalyst.

3. The method of claim 2, wherein the method further comprises:

d) converting the carboxyl ester group to a free carboxyl group, a carboxylic salt, or an amide.

* * * * *